United States Patent [19]

Toda et al.

[11] Patent Number: 5,041,620
[45] Date of Patent: Aug. 20, 1991

[54] METHOD FOR PRODUCING OPTICALLY ACTIVE 2-CYCLOPENTEN-4-ONE-1-OL ESTERS, 2-CYCLOPENTENO-4-ONE-1-OL ESTER AND COMPLEXES THEREOF WITH OPTICALLY ACTIVE 1,6-DIPHENYL-2,4-HEXADIYNE-1,6-DIOL

[75] Inventors: Fumio Toda, Ehime; Masayoshi Minai, Moriyama, both of Japan

[73] Assignee: Sumitomo Chemical Company, Limited, Osaka, Japan

[21] Appl. No.: 892,103

[22] Filed: Aug. 4, 1986

[30] Foreign Application Priority Data

Aug. 10, 1985 [JP] Japan .................................. 60-176130
Feb. 26, 1986 [JP] Japan .................................. 61-40641
Feb. 26, 1986 [JP] Japan .................................. 61-40642

[51] Int. Cl.$^5$ ................... C07C 67/00; C07C 69/013; C07C 69/708; C07C 33/38
[52] U.S. Cl. .................................. 560/187; 260/408; 260/410; 560/220; 560/228; 560/231; 568/807; 568/808; 568/809
[58] Field of Search .................. 260/410, 408; 560/187, 560/231, 220, 228

[56] References Cited

U.S. PATENT DOCUMENTS

| | | | |
|---|---|---|---|
| 4,132,726 | 1/1979 | Kurozumi et al. | 560/231 X |
| 4,229,592 | 10/1980 | Mitscher et al. | 560/231 X |
| 4,571,436 | 2/1986 | Umemura et al. | 560/231 X |

Primary Examiner—Vivian Garner
Attorney, Agent, or Firm—Stevens, Davis, Miller & Mosher

[57] ABSTRACT

A method for producing an optically active 2-cyclopenten-4-one-1-ol ester useful as an intermediate for medicines, agricultural chemicals and represented by the general formula (I),

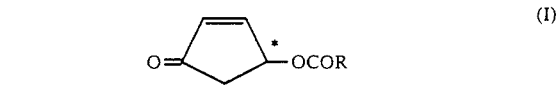

wherein R represents a saturated or unsaturated aliphatic hydrocarbon residue which may or may not be substituted with a halogen atom, and a mark * represents an asymmetric carbon, which comprises bringing a 2-cyclopenten-4-one-1-ol ester represented by the general formula

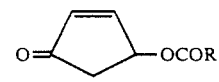

wherein R represents a saturated or unsaturated aliphatic hydrocarbon residue which may or may not be substituted with a halogen atom, into contact with an optically active 1,6-diphenyl-2,4-hexadiyne-1,6-diol derivative represented by the general formula (II),

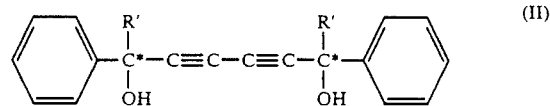

wherein R' represents a halogenated phenyl, lower alkylphenyl, naphthyl or tertiary lower alkyl group, and a mark * represents an asymmetric carbon, in an organic solvent to obtain an optically active cyclopentenone ester complex which is a bound product of the optically active 2-cyclopenten-4-one-1-ol ester represented by the foregoing general formula (I) with the optically active 1,6-diphenyl-2,4-hexadiyne-1,6-diol derivative represented by the foregoing general formula (II), and then decomposing the resulting optically active cyclopentenone ester complex.

43 Claims, No Drawings

METHOD FOR PRODUCING OPTICALLY ACTIVE 2-CYCLOPENTEN-4-ONE-1-OL ESTERS, 2-CYCLOPENTENO-4-ONE-1-OL ESTER AND COMPLEXES THEREOF WITH OPTICALLY ACTIVE 1,6-DIPHENYL-2,4-HEXADIYNE-1,6-DIOL

The present invention relates to a method for producing optically active 2-cyclopenten-4-one-1-ol esters represented by the general formula (I),

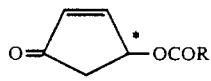

wherein R represents a saturated or unsaturated aliphatic hydrocarbon residue which may or may not be substituted with a halogen atom, and a mark * represents an asymmetric carbon.

Further, the present invention relates to an optically active cyclopentenone ester complex which is a host-guest complex of an optically active 2-cyclopenten-4-one-1-ol ester represented by the general formula (I),

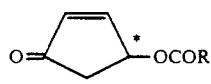

wherein R represents a saturated or unsaturated aliphatic hydrocarbon residue which may or may not be substituted with a halogen atom, and a mark * represents an asymmetric carbon,
with an optically active 1,6-diphenyl-2,4-hexadiyne-1,6-diol derivative represented by the general formula (II),

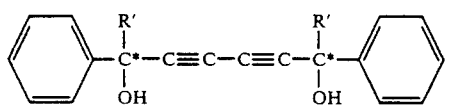

wherein R' represents a halogenated phenyl, lower alkylphenyl, naphthyl or tertiary lower alkyl group, and a mark * represents an asymmetric carbon, and production thereof.

Hitherto, the above optically active cyclopentenone ester complex is not known at all, and the present inventors were the first to find it a novel compound.

Hitherto, it is not also known at all that the optically active 1,6-diphenyl-2,4-hexadiyne-1,6-diol derivative represented by the general formula (II) forms a stable complex by selectively taking either one only of the optically active compounds of a 2-cyclopenten-4-one-1-ol ester represented by the general formula (III),

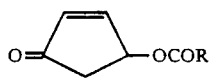

wherein R represents a saturated or unsaturated aliphatic hydrocarbon residue which may or may not be substituted with a halogen atom.

The optically active 2-cyclopenten-4-one-1-ol ester represented by the general formula (I) is an important compound as an intermediate for medicines, agricultural chemicals, etc., and particularly, said ester of R(+)-conformation is very important as a material for prostaglandin derivatives having various physiological activities. The optically active cyclopentenone ester complex of the present invention, on being decomposed, easily produces the optically active 2-cyclopenten-4-one-1-ol ester represented by the general formula (I), so that it is very useful as a material therefor.

The present invention provides the foregoing optically active cyclopentenone ester complex which is a useful material for such optically active 2-cyclopenten4-one-1-ol ester and production thereof.

The present inventors extensively studied a method for producing the optically active 2-cyclopenten4-one-1-ol ester easily in industry as well as in high optical purities and in good yields, and as a result, completed the present invention.

The present invention provides a method for producing an optically active 2-cyclopenten-4-one-1-ol ester represented by the general formula (1),

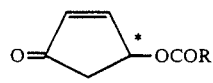

wherein R represents a saturated or unsaturated aliphatic hydrocarbon residue which may or may not be substituted with a halogen atom, and a mark * represents an asymmetric carbon,
which comprises bringing a 2-cyclopenten-4-one-1-ol ester represented by the general formula (III),

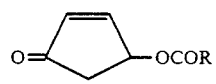

wherein R represents a saturated or unsaturated aliphatic hydrocarbon residue which may or may not be substituted with a halogen atom, into contact with an optically active 1,6-diphenyl-2,4-hexadiyne-1,6-diol derivative represented by the general formula (II),

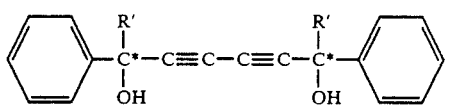

wherein R' represents a halogenated phenyl, lower alkylphenyl, naphthyl or tertiary lower alkyl group, and a mark * represents an asymmetric carbon,
in an organic solvent to obtain an optically active cyclopentenone ester complex which is a host-guest complex of the optically active 2-cyclopenten-4-one-1-ol ester represented by the foregoing general formula (I) with the optically active 1,6-diphenyl-2,4-hexadiyne1,6-diol derivative represented by the foregoing general formula (II), and then decomposing the resulting optically active cyclopentenone ester complex.

The foregoing optically active cyclopentenone ester complex which is an object of the present invention can easily be obtained by bringing the 2-cyclopenten4-one-1-ol ester represented by the foregoing general formula (III) into contact with the optically active 1,6-diphenyl-2,4-hexadiyne-1,6-diol derivative represented by the foregoing general formula (II) in an organic solvent.

In the present invention, the 2-cyclopenten-4-one-1-ol ester, a starting material, can easily be produced, for example, by reacting 2-cyclopenten-4-one-1-ol with the acid halide (e.g. acid chloride) of a saturated or unsaturated carboxylic acid which may or may not be substituted with a halogen atom in the presence of a base.

Such 2-cyclopenten-4-one-1-ol ester includes the esters with the following acids: acetic acid, propionic acid, n-butyric acid, isobutyric acid, n-valeric acid, isovaleric acid, pivalic acid, methylethylacetic acid, n-caproic acid, isocaproic acid, β-methylvaleric acid, tert-butylacetic acid, diethylacetic acid, methyl-n-propylacetic acid, methylisopropylacetic acid, 2-methylbutane-2-carboxylic acid, heptanoic acid, caprylic acid, chloroacetic acid, bromoacetic acid, dichloroacetic acid, β-chloropropionic acid, γ-chlorobutyric acid, trichloroacetic acid, crotonic acid, 4-pentenoic acid, 2-pentenoic acid, acrylic acid, 4-pentynoic acid, methoxyacetic acid, ethoxyacetic acid, methoxypropionic acid, ethoxypropionic acid, etc.

The optically active 1,6-diphenyl-2,4-hexadiyne1,6-diol derivative represented by the foregoing general formula (II) which is the other starting material can easily be synthesized, for example, by the method described in Japanese Patent Application Kokai (Laid-open) No. 22469/1984.

In the general formula (II), specific examples of a substituent R' include a chlorophenyl, bromophenyl, fluorophenyl, naphthyl, toluyl, ethylphenyl, tert-butyl and tert-amyl groups, etc.

The optically active cyclopentenone ester complex can be produced by bringing the 2-cyclopenten4-one-1-ol ester into contact with the optically active 1,6-diphenyl-2,4-hexadiyne-1,6-diol derivative (hereinafter referred to as optically active diynediol) in an organic solvent to deposit a complex which is a host-guest complex of either one of the optically active compounds of 2-cyclopenten-4-one-1-ol ester with the optically active diynediol and then separating the resulting complex.

In this reaction, the 2-cyclopenten-4-one-1-ol ester may be any of the racemate, optically active compounds and optically active mixtures containing either one of the optically active compounds in excess. However, in order to obtain the optically active 2-cyclopenten4-one-1-ol ester by decomposition of the resulting complex, it is advantageous in practice to use the racemate or optically active mixtures containing either one of the optically active bodies in excess.

The amount of the raw ester, used as a material in this reaction, is properly selected according to the content of the optically active complex-forming 2-cyclopenten-4-one-1-ol ester contained in the raw ester. Generally, however, it is such an amount that the content of said optically active complex-forming 2-cyclopenten-4-one-1-ol ester is 0.75 to 2 times by equivalent, preferably 1 to 2 times by equivalent based on the optically active diynediol. When the raw ester is a racemate, therefore, its amount is 1.5 to 4 times by equivalent, preferably 2 to 4 times by equivalent based on the optically active diynediol.

For the optically active diynediol used in this complex formation, the compound having a substituent R' is used as described above. However, when the complex-forming ability, yield, optical purity of the optically active 2-cyclopenten-4-one-1-ol ester obtained by decomposition of the complex, etc. are taken into account, optically active diynediol in which the substituent R' is a bromophenyl, chlorophenyl or fluorophenyl group are preferably used.

Also, among the 2-cyclopenten-4-one-1-ol esters given above, the following ones are particularly preferably used because they form the complex in good efficiency and give good yields: the esters with acids such as propionic acid, butyric acid, isobutyric acid, valeric acid, isovaleric acid, pivalic acid, caproic acid, isocaproic acid, chloroacetic acid, bromoacetic acid, dichloroacetic acid, β-chloropropionic acid, γ-chlorobutyric acid and methoxyacetic acid.

For the organic solvent used for complex formation, there are given solvents inactive to reaction such as ethyl ether, benzene, toluene, acetonitrile, ethyl acetate, carbon tetrachloride, chloroform, dichloromethane, dichloroethane, haxane, petroleum ether, ligroin, etc. These solvents may be used alone or in combination.

Any reaction temperature in a range of from $-20°$ C. to the boiling point of the solvent used may be used, but generally, the reaction temperature is in a range of from $0°$ to $80°$ C. According to the method described above, when the 2-cyclopenten-4-one-1-ol ester, a raw ester, and optically active diynediol are brought into contact with each other in the organic solvent, either one of the optically active compounds contained in the raw ester is easily bonded to the optically active diynediol to form chiefly a 1:1 complex.

When this reaction solution is cooled, or a solvent not dissolving the resulting complex (e.g. hexane, petroleum ether) is added thereto, the complex is deposited as crystals. By separating the crystals, the objective complex, a host-guest complex of the optically active 2-cyclopenten-4-one-1-ol ester with the optically active diynediol, can be obtained in good optical purities and in good yields. If necessary, the complex obtained may be purified by recrystallization, etc. according to the method described above.

By decomposing the optically active cyclopentenone ester complex thus obtained, the optically active 2-cyclopenten-4-one-1-ol ester can be obtained.

For decomposing the complex, methods such as heating under reduced pressure or treatment by column chromatography are employed.

In the method of heating under reduced pressure, the level of reduced pressure and the heating temperature are properly selected according to the condition of the method. Generally, however, the pressure is about 1 to about 100 mmHg, and the heating temperature is one at which the optically active 2-cyclopenten-4-one-1-ol ester can be distilled out under that pressure.

Also, for the solvent used in column chromatography, one or more are properly selected from solvents including the reaction solvents given above according to the optically active 2-cyclopenten-4-one-1-ol ester.

Alternatively, for separation of the optically active 2-cyclopenten 4-one-1-ol ester from the optically active cyclopentenone ester complex, the following method is applied: Said ester complex is treated with a guest molecule easily capable of replacing the optically active 2-cyclopenten-4-one-1-ol ester to crystallize the complex of the optically active diynediol with the guest molecule, and then the optically active 2-cyclopenten4-one-1-ol ester liberated from said ester complex is recovered.

Generally, this method is carried out as follows: The optically active cyclopentenone ester complex and the guest molecule are treated in an organic solvent to crystallize the complex of the optically active diynediol with the guest molecule, the resulting complex is filtered off and then the optically active 2-cyclopenten-4-one-1-ol ester is recovered from the filtrate.

For the guest molecule, the followings may be given: ketones (e.g. acetone, methyl ethyl ketone, cyclopentanone, cyclohexanone), cyclic ethers (e.g. tetrahydrofuran, dioxane), heterocyclic amines (e.g. pyridine, quinoline), dimethyl sulfoxide, N,N-dimethylformamide, aliphatic amines, alicyclic amines, aldehydes, cyclic amides (e.g. pyrrolidone) and aromatic amines. But, the guest molecule of the present invention is not limited thereto if it is capable of replacing the optically active 2-cyclopenten-4-one-1-ol ester.

For the solvent used in this method, there are given the foregoing solvents used to form the optically active cyclopentenone ester complex, i.e. solvents inactive to this reaction such as ethyl ether, benzene, toluene, acetonitrile, ethyl acetate, carbon tetrachloride, chloroform, dichloromethane, dichloroethane, hexane, heptane, petroleum ether, ligroin, etc. These solvents may be used alone or in combination.

Any reaction temperature in a range of from $-20°$ C. to the boiling point of the solvent used may be used, but generally, the reaction temperature is in a range of from $-10°$ C. to $100°$ C.

According to the method described above, when the optically active cyclopentenone ester complex and the guest molecule are brought into contact with each other in the organic solvent, the guest molecule is easily bonded to the optically active diynediol to form the complex, whereby the optically active 2-cyclopenten4-one-1-ol ester is liberated from the ester complex.

When this reaction solution is cooled, or a solvent not dissolving the resulting complex (e.g. hexane, petroleum ether) is added thereto, the complex is deposited as crystals. By filtering off the complex and treating the filtrate as usual, the objective optically active 2-cyclopenten-4-one-1-ol ester can be obtained in good yields. In this method, there is no need to dissolve the optically active cyclopentenone ester complex, the same result being also obtained by merely heat-treating the ester complex crystals themselves and the guest molecule.

The amount of the guest molecule needs to be larger than that theoretically necessary to form the complex of the optically active diynediol with the guest molecule, and it is generally one equivalent or more, preferably 2 to 30 times by equivalents based on optically active 1,6-diphenyl-2,4-hexadiyne-1,6-diol derivative.

According to the method described above, both the optically active 2-cyclopenten-4-one-1-ol ester and the optically active diynediol can be obtained in good yields.

By the decomposition treatment described above, the objective optically active 2-cyclopenten-4-one-1-ol ester represented by the general formula (I) can be obtained in good optical purities and in good yields.

The optically active diynediol recovered by such decomposition treatment can be re-used after purified by recrystallization, etc. if necessary.

In forming the complex of the optically active diynediol with the optically active 2-cyclopenten-4-one-1-ol ester according to the method of the present invention, which of the optically active compounds of the latter is selected to form the complex is determined by the optical conformation of the former. Consequently, by properly determining the optical conformation of the former and decomposing the resulting complex, optically active 2-cyclopenten-4-one-1-ol esters having any of the S- and R-conformation can be obtained.

Consequently, this reaction can be used as follows to obtain the optically active 2-cyclopenten-4-one-1-ol esters different in the optical conformation from each other. When the raw ester is a racemate or an optically active mixture containing either one of the optically active bodies in optical excess, the reaction solution from which the complex produced by the complex formation has been removed (e.g. a filtrate after removal of the complex by filtration) contains an optical excess of the optically active 2-cyclopenten-4-one-1-ol ester which is left unreacted and has an optical conformation opposite to that of the ester used for the previous complex formation. Consequently, the optically active 2-cyclopenten-4-one-1-ol ester having an optical conformation opposite to that of the ester previously obtained can be obtained, for example, by concentrating the filtrate, distilling the residue by heating under reduced pressure to recover said ester left unreacted, bringing the ester into contact with the optically active diynediol having an optical conformation opposite to that of the previous diynediol according to the same condition as in the previous complex formation, and decomposing the resulting complex.

Thus, by the method of the present invention, the optically active cyclopentenone ester complex, which is a host-guest complex of the optically active 2-cyclopenten-4-one-1-ol ester represented by the foregoing general formula (I) with the optically active diynediol represented by the foregoing general formula (II), can be obtained in high optical purities and in good yields. Similarly, the optically active 2-cyclopenten-4-one-1-ol ester represented by the general formula (I) can also be produced easily in industry as well as in high optical purities and in good yields. Said ester complex is very useful as a material for the optically active 2-cyclopenten-4-one-1-ol ester. Also, the method of the present invention is very useful as a method for the optical resolution of 2-cyclopenten-4-one-1-ol esters.

The present invention will be illustrated with reference to the following examples, but it is not limited to these examples.

REFERENCE EXAMPLE 1

To a solution of 9.8 g of racemic 2-cyclopenten4-one-1-ol in 50 ml of benzene were added 10.7 g of n-butyryl chloride and 7.9 g of pyridine. After standing at room temperature for 12 hours, 50 ml of water was added to allow the benzene layer to separate from the solution. The benzene layer was taken, washed with water, dried over anhydrous sodium sulfate and distilled under reduced pressure to obtain 16.0 g of racemic 2-cyclopenten-4-one-1-ol n-butyric acid ester having a boiling point of $134°$ C./23 mmHg.

EXAMPLE 1

To a solution of 4.83 g of $(-)$-1,6-diphenyl-1,6-di(o-chlorophenyl)-2,4-hexadiyne-1,6-diol $\{[\alpha]_D^{20}, -122°$ (methanol, c=1.0)$\}$ in a mixed solvent of 5 ml of ether and 10 ml of petroleum ether was added 3.36 g of the racemic 2-cyclopenten-4-one-1-ol n-butyric acid ester, and the mixture was allowed to stand at room temperature for 12 hours.

The deposited crystals were collected by filtration to obtain 4.69 g of a colorless and prism-like product which was a 1:1 crude complex of $(-)$-1,6-diphenyl1,6-di(o-chlorophenyl)-2,4-hexadiyne-1,6-diol and $(-)$2- cyclopenten-4-one-1-ol n-butyric acid ester. This crude complex was once recrystallized from a mixed solvent of 5 ml of ether and 10 ml of petroleum ether to obtain 3.84 g of the complex. This complex was heated under reduced pressure to obtain 0.94 g of (−)-cyclopenten4-one-1-ol n-butyric acid ester.

Boiling point, 134° C./23 mmHg
$[\alpha]_D^{20}$, 107° (methanol, c=1.0)

The filtrate, obtained by collecting the 1:1 crude complex by filtration, was distilled under reduced pressure to obtain 2.05 g of crude (+)-2-cyclopenten-4-one-1-ol n-butyric acid ester. Thereafter, 2.05 g of this crude ester and 5.89 g of (+)-1,6-diphenyl-1,6-di (o-chlorophenyl)-2,4-hexadiyne-1,6-diol {$[\alpha]_D^{20}$, +122° (methanol, c=1.0)} were dissolved in a mixed solvent of 5 ml of ether and 10 ml of petroleum ether and allowed to stand at room temperature for 12 hours.

The deposited crystals were collected by filtration to obtain 4.95 g of a colorless and prism-like product which was a 1:1 crude complex of (+)-1,6-diphenyl-1,6-di(o-chlorophenyl)-2,4-hexadiyne-1,6-diol and (+)-2-cyclopenten-4-one-1-ol n-butyric acid ester. This crude complex was once recrystallized from a mixed solvent of 5 ml of ether and 10 ml of petroleum ether to obtain 4.10 g of the complex. This complex was heated under reduced pressure to obtain 0.94 g of (+)-2-cyclopenten-4-one 1-ol n-butyric acid ester.

Boiling point, 134° C./23 mmHg
$[\alpha]_D^{20}$, +107° (methanol, c=1.0)

EXAMPLES 2 to 6

Reaction and after-treatment were carried out in the same manner as in Example 1 except that equimolar amounts of the raw esters shown in Table 1 were used in place of 2-cyclopenten-4-one-1-ol n-butyric acid ester, to obtain the optically active esters shown in Table 1.

1,6-di(o-chlorophenyl)-2,4-hexadiyne-1,6-diol, 10.45 g of (±)-2-cyclopenten-4-one-1-ol n-butyric acid ester and 15 ml of dichloromethane, and the mixture was heated to 40° C. to turn it into a solution.

Thereafter, 35 ml of hexane was added at the same temperature, and the temperature of the solution was maintained for 30 minutes, lowered to 20° C. and kept at that temperature for 2 hours.

The deposited white crystals were collected by filtration to obtain 13.7 g of a 1:1 complex of (+)-1,6-diphenyl-1,6-di(o-chlorophenyl)-2,4-hexadiyne-1,6-diol with (+)-2-cyclopenten-4-one-1-ol n-butyric acid ester.
m.p., 110°–112° C.
$[\alpha]_D^{20}$, +121.5° (c=1, methanol)

Thereafter, 13.5 g of the complex thus obtained was distilled by heating under reduced pressure to obtain 3.31 g of (+)-2-cyclopenten-4-one-1-ol n-butyric acid ester.
b.p., 134° C./23 mmHg
$[\alpha]_D^{20}$, +107.2° (c=1, methanol)

EXAMPLE 8

To the same flask as used in Example 7 were added 4.83 g of (+)-1,6-diphenyl-1,6-di(o-chlorophenyl)2,4-hexadiyne-1,6-diol, 3.72 g of (±)-2-cyclopenten-4-one-1-ol chloroacetic acid ester and 12 ml of dichloromethane, and the mixture was heated to 40° C. to turn it into a solution. Thereafter, 15 ml of petroleum ether was added at 35° to 40° C., and the solution was cooled to 20° C. and kept at the same temperature for 2 hours.

The deposited white crystals were collected by filtration to obtain 4.61 g of a complex of (+)-1,6-diphenyl-1,6-di(o-chlorophenyl)-2,4-hexadiyne-1,6-diol with (+)-2-cyclopenten-4-one-1-ol chloroacetic acid ester.
m.p., 108°–110° C.
$[\alpha]_D^{20}$, +110.8° (c=1, methanol)

Thereafter, 4.3 g of the complex thus obtained was

TABLE 1

| Example | Raw ester Name of compound | Raw ester Structural formula | bp 23 mm Hg | Optically active ester Physical property $[\alpha]_D^{20}$ MeOH c = 1.0 |
|---|---|---|---|---|
| 2 | 2-Cyclopenten-4-one-1-ol n-propionic acid ester | O=⟨⟩—OCOCH$_2$CH$_3$ | 127° C. | (+) +99°<br>(−) −99° |
| 3 | 2-Cyclopenten-4-one-1-ol isobutyric acid ester | O=⟨⟩—OCOCH(CH$_3$)$_2$ | 128° C. | (+) +107°<br>(−) −107° |
| 4 | 2-Cyclopenten-4-one-1-ol n-valeric acid ester | O=⟨⟩—OCO(CH$_2$)$_3$CH$_3$ | 145° C. | (+) +104°<br>(−) −104° |
| 5 | 2-Cyclopenten-4-one-1-ol isovaleric acid ester | O=⟨⟩—OCOCH$_2$CH(CH$_3$)CH$_3$ | 140° C. | (+) +112°<br>(−) −112° |
| 6 | 2-Cyclopenten-4-one-1-ol pivalic acid ester | O=⟨⟩—OCOC(CH$_3$)$_3$ | 129° C. | (+) +111°<br>(−) −111° |

EXAMPLE 7

To a four-necked flask equipped with a stirrer and a thermometer were added 12.6 g of (+)-1,6-diphenylcolumn-chromatographed with a 10:2 mixed solvent of toluene and ethyl acetate as a developing solvent, to obtain 1.1 g of (+)-2-cyclopenten-4-one-1-ol chloroacetic acid ester.
m.p., 74°-75° C.
$[\alpha]_D^{20}$, +103° (c=1, methanol)

EXAMPLES 9 to 11

Reaction and after-treatment were carried out in the same manner as in Example 8 except that the raw esters shown in Table 2 were used in place of 2-cyclopenten-4-one-1-ol chloroacetic acid ester, to obtain the optically active esters shown in Table 2.

TABLE 2

| | Raw ester | | Intermediate complex | | Optically active ester | |
|---|---|---|---|---|---|---|
| Example | Compound | Amount used | Physical property | Yield | Physical property | Yield |
| 9 | 2-Cyclopenten-4-one-1-ol bromoacetic acid ester | 4.38 g | m.p. 110-113° C. $[\alpha]_D^{20}$, +112.5° (c = 1, methanol) | 5.27 g | m.p. 61-63° C. $[\alpha]_D^{20}$, +97.8° (c = 1, methanol) | 1.58 g |
| 10 | 2-Cyclopenten-4-one-1-ol β-chloropropionic acid ester | 4.34 | m.p. 85-87° C. $[\alpha]_D^{20}$, +122° (c = 1, methanol) | 4.56 | $n_D^{20}$ 1.4893 $[\alpha]_D^{20}$, +76.5° (c = 1, methanol) | 1.22 |
| 11 | 2-Cyclopenten-4-one-1-ol γ-chlorobutyric acid ester | 3.05 | m.p. 82-84° C. $[\alpha]_D^{20}$, +118.8° (c = 1, methanol) | 4.66 | $n_D^{20}$ 1.4908 $[\alpha]_D^{20}$, +86.8° (c = 1, methanol) | 1.31 |

EXAMPLE 12

To the same flask as used in Example 8 were added 4.83 g of (+)-1,6-diphenyl-1,6-di(o-chlorophenyl)-2,4-hexadiyne-1,6-diol, 3.40 g of (±)-2-cyclopenten-4-one-1-ol methoxyacetic acid ester and 12 ml of dichloromethane, and the mixture was heated to 40° C. to turn it into a solution. Thereafter, 10 ml of petroleum ether was added at 35° to 40° C., and the solution was cooled to 20° C. and kept at the same temperature for 2 hours.

The deposited white crystals were collected by filtration to obtain 5.55 g of a complex of (+)-1,6-diphenyl-1,6-di(o-chlorophenyl)-2,4-hexadiyne-1,6-diol with (+)-2-cyclopenten-4-one-1-ol methoxyacetic acid ester.
m.p., 120-121° C.
$[\alpha]_D^{20}$, +117 1° (c=1, methanol)

Thereafter, 5 g of the complex thus obtained was distilled by heating under reduced pressure to obtain 1.4 g of (+)-2-cyclopenten-4-one-1-ol methoxyacetic acid ester.
$[\alpha]_D^{20}$, +97.4° (c=1, methanol)
$n_D^{20}$, 1.4811

REFERENCE EXAMPLE 2

To a solution of 9.8 g of racemic 2-cyclopenten-4-one-1-ol in 50 ml of benzene were added 10.7 g of n-butyryl chloride and 7.9 g of pyridine. After standing at room temperature for 12 hours, 50 ml of water was added to allow the benzene layer to separate from the solution. The benzene layer was taken, washed with water, dried over anhydrous sodium sulfate and distilled under reduced pressure to obtain 16.0 g of racemic 2-cyclopenten-4-one-1-ol n-butyric acid ester having a boiling point of 134° C./23 mmHg.

EXAMPLE 13

To a solution of 4.83 g of (−)-1,6-diphenyl-1,6-di(o-chlorophenyl)-2,4-hexadiyne-1,6-diol $\{[\alpha]_D^{20}$, −122° (methanol, c=1.0)} in a mixed solvent of 5 ml of ether and 10 ml of petroleum ether was added 3.36 g of the racemic 2-cyclopenten-4-one-1-ol n-butyric acid ester, and the mixture was allowed to stand at room temperature for 12 hours.

The deposited crystals were collected by filtration to obtain 4.69 g of a colorless and prism-like product which was a 1:1 crude complex of (−)-1,6-diphenyl-1,6-di (o-chlorophenyl)-2,4-hexadiyne-1,6-diol and (−)-2-cyclopenten-4-one-1-ol n-butyric acid ester. This crude complex was once recrystallized from a mixed solvent of 5 ml of ether and 10 ml of petroleum ether to obtain 3.84 g of the complex.
m p., 110°-112° C.
$]\alpha]_D^{20}$, −121.4° (c=1, methanol)

The filtrate, obtained when the above crude complex was collected by filtration, was concentrated, and the residue was distilled under reduced pressure to obtain 2.05 g of crude (+)-2-cyclopenten-4-one-1-ol n-butyric acid ester. Thereafter, 2.05 g of this crude ester and 5.89 g of (+)-1,6-diphenyl-1,6-di(o-chlorophenyl)-2,4-hexadiyne-1,6-diol $\{[\alpha]_D^{20}$, +122° (methanol, c=1.0)} were dissolved in a mixed solvent of 5 ml of ether and 10 ml of petroleum ether and allowed to stand at room temperature for 12 hours.

The deposited crystals were collected by filtration to obtain 4.95 g of a colorless and prism-like product which was a 1:1 crude complex of (+)-1,6-diphenyl-1,6-di(o-chlorophenyl)-2,4-hexadiyne-1,6-diol and (+)-2-cyclopenten-4-one-1-ol n-butyric acid ester. This crude complex was once recrystallized from a mixed solvent of 5 ml of ether and 10 ml of petroleum ether to obtain 4.10 g of the complex.
m.p., 111-112° C.
$[\alpha]_D^{20}$, +121.2° (c=1, methanol)

EXAMPLES 14 to 16

Reaction and after-treatment were carried out in the same manner as in Example 13 except that equimolar amounts of the racemic raw esters shown in Table 3 were used in place of racemic 2-cyclopenten-4-one-1-ol n-butyric acid ester, to obtain the results shown in Table 3.

TABLE 3

| | | Formed complex | | | |
|---|---|---|---|---|---|
| Example | Raw ester | Components constituting the complex | Physical property | Components constituting the complex | Physical property |
| 14 | HCP n-valeric acid ester | (−)-Diynediol and (−)-HCP n-valeric acid ester | $[\alpha]_D^{20}$ −118° m.p. 95-96° C. | (+)-Diynediol and (+)-HCP n-valeric acid ester | $[\alpha]_D^{20}$ +118° m.p. 95.5-96.5° C. |

TABLE 3-continued

| Example | Raw ester | Formed complex | | | |
|---|---|---|---|---|---|
| | | Components constituting the complex | Physical property | Components constituting the complex | Physical property |
| 15 | HCP isovaleric acid ester | (−)-Diynediol and (−)-HCP isovaleric acid ester | $[\alpha]_D^{20}$ −118° m.p. 108–110° C. | (+)-Diynediol and (+)-HCP isovaleric acid ester | $[\alpha]_D^{20}$ +117.5° m.p. 108–109° C. |
| 16 | HCP pivalic acid ester | (−)-Diynediol and (−)-HCP pivalic acid ester | $[\alpha]_D^{20}$ −114° m.p. 113–115° C. | (+)-Diynediol and (+)-HCP pivalic acid ester | $[\alpha]_D^{20}$ +115° m.p. 114–116° C. |

HCP: 2-Cyclopenten-4-one-1-ol
Diynediol: 1,6-Diphenyl-1,6-di(o-chlorophenyl)-2,4-hexadiyne-1,6-diol

EXAMPLE 17

To a four-necked flask equipped with a stirrer and a thermometer were added 12.6 g of (+)-1,6-diphenyl-1,6-di(o-chlorophenyl)-2,4-hexadiyne-1,6-diol, 10.45 g of (±)-2-cyclopenten-4-one-1-ol n-butyric acid ester and 15 ml of dichloromethane, and the mixture was heated to 40° C. to turn it into a solution. Thereafter, 35 ml of hexane was added at the same temperature, and the temperature of the solution was maintained for 30 minutes, lowered to 20° C. and kept at that temperature for 2 hours. The deposited crystals were collected by filtration to obtain 13.7 g of a 1:1 complex of (+)-1,6-diphenyl-1,6-di(o-chlorophenyl)-2,4-hexadiyne-1,6-diol with (+)-2-cyclopenten-4-one-1-ol n-butyric acid ester as a white crystal.
m.p., 110°–112° C.
$[\alpha]_D^{20}$, +121.5° (c=1, methanol)

EXAMPLE 18

To the same flask as used in Example 17 were added 4.83 g of (+)-1,6-diphenyl 1,6-di(o-chlorophenyl)-2,4-hexadiyne-1,6-diol, 3.72 g of (±)-2-cyclopenten-4-one-1-ol chloroacetic acid ester and 12 ml of dichloromethane, and the mixture was heated to 40° C. to turn it into a solution. Thereafter, 15 ml of petroleum ether was added at 35° to 40° C., and the solution was cooled to 20° C. and kept at the same temperature for 2 hours. The deposited white crystals were collected by filtration to obtain 4.61 g of a complex of (+)-1,6-diphenyl-1,6-di(o-chlorophenyl)-2,4-hexadiyne-1,6-diol with (+)-2-cyclopenten-4-one-1-ol chloroacetic acid ester.
m.p., 108°–110° C.
$[\alpha]_D^{20}$, +110.8° (c=1, methanol)

EXAMPLES 19 to 21

Reaction and after-treatment were carried out in the same manner as in Example 18 except that the racemic raw esters shown in Table 4 were used in place of the racemic 2-cyclopenten-4-one-1-ol chloroacetic acid ester, to obtain the results shown in Table 4.

TABLE 4

| | Raw ester | | Formed complex | | |
|---|---|---|---|---|---|
| Example | Name of compound | Amount used | Components constituting the complex | Yield | Physical property |
| 19 | HCP bromoacetic acid ester | 4.38 g | (+)-Diynediol and (+)-HCP bromoacetic acid ester | 5.27 g | m.p. 110–113° C. $[\alpha]_D^{20}$ +112.5° (c = 1, methanol) |
| 20 | HCP β-chloropropionic acid ester | 4.34 g | (+)-Diynediol and (+)-HCP β-chloropropionic acid ester | 4.56 g | m.p. 85–87° C. $[\alpha]_D^{20}$ +122° (c = 1, methanol) |
| 21 | HCP γ-chlorobutyric acid ester | 4.05 g | (+)-Diynediol and (+)-HCP γ-chlorobutyric acid ester | 4.66 g | m.p. 82–84° C. $[\alpha]_D^{20}$ +118.8° (c = 1, methanol) |

HCP: 2-Cyclopenten-4-one-1-ol
Diynediol: 1,6-Diphenyl-1,6-di(o-chlorophenyl)-2,4-hexadiyne-1,6-diol

EXAMPLE 22

To the same flask as used in Example 18 were added 4.83 g of (+)-1,6-diphenyl-1,6-di(o-chlorophenyl)-2,4-hexadiyne-1,6-diol, 3.40 g of (±)-2-cyclopenten-4-one-1-ol methoxyacetic acid ester and 12 ml of dichloromethane, and the mixture was heated to 40° C. to turn it into a solution. Thereafter, 10 ml of petroleum ether was added at 35° to 40° C., and the solution was cooled to 20° C. and kept at the same temperature for 2 hours.
The deposited white crystals were collected by filtration to obtain 5.55 g of a complex of (+)-1,6-diphenyl-1,6-di(o-chlorophenyl)-2,4-hexadiyne-1,6-diol with (+)-2-cyclopenten-4-one-1-ol methoxyacetic acid ester
m.p., 120°–121° C.
$[\alpha]_D^{20}$, +117.1° (c=1, methanol)

EXAMPLE 23

To a four-necked flask equipped with a stirrer and a thermometer were added 4.83 g of (+)-1,6-diphenyl-1,6-di(o-chlorophenyl)-2,4-hexadiyne-1,6-diol, 50 ml of n-hexane and 3.36 g of (±)-2-cyclopenten-4-one-1-ol n-butyric acid ester. The resulting mixture was heated to 40° to 45° C., kept at the same temperature for 2 to 3 hours, cooled to 20° C., kept at the same temperature for 2 hours and filtered at the same temperature to obtain 6.35 g of a complex of (+)-1,6-diphenyl-1,6-di(o-chlorophenyl)-2,4-hexadiyne-1,6-diol with (+)-2-cyclopenten-4-one-1-ol n-butyric acid ester as a white crystal.
m.p., 106°–109° C.
$[\alpha]_D^{20}$, +118.7° (c=1, methanol)

EXAMPLE 24

To a four-necked flask equipped with a stirrer and a thermometer were added 4.83 g of (+)-1,6-diphenyl-1,6-di(o-chlorophenyl)-2,4-hexadiyne-1,6-diol, 50 ml of n-hexane and 3.36 g of (±)-2-cyclopenten-4-one-1-ol n-butyric acid ester. The resulting mixture was heated to 40° to 45° C., kept at the same temperature for 2 to 3 hours, cooled to 20° C., kept at the same temperature for 2 hours and filtered at the same temperature to obtain 6.38 g of a complex of (+)-1,6-diphenyl-1,6-di(o-chlorophenyl)-2,4-hexadiyne-1,6-diol with (+)-2-cyclopenten-4-one-1-ol n-butyric acid ester as a white crystal.

m.p., 106°–109° C.

$[\alpha]_D^{20}$, +118.7° (c = 1, methanol)

A mixture of 6 g of this crystal and 6 ml of dichloromethane was heated to 40° C. to turn it into a solution. After adding 36 ml of hexane at the same temperature, the mixture was kept at the same temperature for 30 minutes, cooled to 20° C., kept at the same temperature for 1 hour and filtered at the same temperature to obtain 6.0 g of a complex of (+)-1,6-diphenyl-1,6-di(o-chlorophenyl)-2,4-hexadiyne-1,6-diol with (+)-2-cyclopenten-4-one-1-ol n-butyric acid ester as a white crystal.

m.p., 110°–112° C.

$[\alpha]_D^{20}$, +121.4° (c = 1, methanol)

EXAMPLE 25

Using the same apparatus as used in Example 24, procedure was carried out in the same manner as in Example 24 except that n-hexane was replaced by n-heptane, to obtain 6.25 g of a complex.

m.p., 106°–109° C.

$[\alpha]_D^{20}$, +119° (c = 1, methanol)

In the same manner as in Example 24, a mixture of this crystal and dichloromethane was heated to turn it into a solution, and n-heptane was added to the solution to form crystals, which were then filtered off to obtain 5.9 g of a complex of (+)-1,6-diphenyl-1,6-di(o-chlorophenyl)-2,4-hexadiyne-1,6-diol with (+)-2-cyclopenten-4-one-1-ol n-butyric acid ester as a white crystal.

m.p., 110°–112° C.

$[\alpha]_D^{20}$, +121.4° (c = 1, methanol)

EXAMPLE 26

To a four-necked flask equipped with a stirrer and a thermometer were added 75.6 g of (+)-1,6-diphenyl-1,6-di(o-chlorophenyl)-2,4-hexadiyne-1,6-diol, 62.7 g of (±)-2-cyclopenten-4-one-1-ol n-butyric acid ester and 90 ml of dichloromethane, and the resulting mixture was heated to 40° C. to turn it into a solution. After adding 210 ml of hexane at the same temperature, the mixture was kept at the same temperature for 30 minutes, cooled to 20° C. and kept at the same temperature for 2 hours. Deposited crystals were filtered off to obtain 82.5 g of a 1:1 complex of (+)-1,6-diphenyl-1,6-di(o-chlorophenyl)-2,4-hexadiyne-1,6 diol with (+)-2-cyclopenten-4-one-1-ol n-butyric acid ester as a white crystal.

m.p., 110°–112° C.

$[\alpha]_D^{20}$, +121.5° (c = 1, methanol)

To a four-necked flask equipped with a stirrer and a thermometer were added 10 g of this complex of (+)-1,6-diphenyl-1,6-di(o-chlorophenyl)-2,4-hexadiyne-1,6-diol with (+)-2-cyclopenten-4-one-1-ol n-butyric acid ester and 8 g of acetone, and the mixture was heated under reflux for 3 hours. After adding 50 ml of n-hexane at the same temperature, the mixture as cooled to 0° to 5° C., kept at the same temperature for 0.5 to 1.0 hour and filtered to obtain 9.2 g of a 1:2 complex of (+)-1,6-diphenyl-1,6-di (o-chlorophenyl)-2,4-hexadiyne-1,6-diol with acetone as a white crystal.

m.p., 100.4° C.

This crystal was treated at 60° C. under a reduced pressure of 20 mmHg to obtain 7.4 g of (+)-1,6-diphenyl-1,6-di (o-chlorophenyl)-2,4-hexadiyne 1,6-diol (percent recovery, 99.7%).

m.p., 131.8° C.

$[\alpha]_D^{20}$, +124.6° (c = 1, methanol)

The filtrate obtained when the above complex was collected by filtration was concentrated, and the residue was distilled under reduced pressure to obtain 5 g of (+)-2-cyclopenten-4-one 1-ol n-butyric acid ester (percent recovery, 96.9%).

$[\alpha]_D^{20}$, +107.2° (c = 1, methanol)

EXAMPLES 27 to 32

The complex of (+)-1,6-diphenyl-1,6-di(o-chlorophenyl)-2,4-hexadiyne-1,6-diol with (+)-2-cyclopenten-4-one-1-ol n-butyric acid ester obtained in Example 26 was treated in the same manner as in Example 26 except that the kind and amount of the exchanging guest were changed, to obtain the results shown in Table 5.

TABLE 5

| Example | Exchanging guest Kind | Amount (g) | Complex formed m.p. (°C.) | (+)-n-Butyric acid ester Percent recovery (%) | $[\alpha]_D^{20}$ (c = 1, methanol) | (+)-AAD* Percent recovery (%) | m.p. (°C.) | $[\alpha]_D^{20}$ (c = 1, methanol) |
|---|---|---|---|---|---|---|---|---|
| 27 | Cyclopentanone | 11.6 | 106 | 100 | +107.2° | 100 | 131.5 | +124.5° |
| 28 | Tetrahydrofuran | 10.0 | 117 | 90 | +107.0° | 90 | 131.4 | +123° |
| 29 | Pyridine | 10.9 | 90 | 100 | +106.5° | 94 | 131.5 | +124° |
| 30 | Dimethyl sulfoxide | 10.8 | — | 100 | +106.8° | 99 | 131.3 | +124.2° |
| 31 | N,N-dimethylformamide | 10.1 | — | 100 | +107.0° | 97 | 131.5 | +124° |
| 32 | Acetone | 15 | 100.5 | 100 | +107.4° | 95 | 131.8 | +124.3° |

*(+1)-1,6-Diphenyl-1,6-di(o-chlorophenyl)-2,4-hexadiyne-1,6-diol

EXAMPLE 33

To the same flask as used in Example 26 were added 14.49 g of (+)-1,6-diphenyl-1,6-di(o-chloro-phenyl)-2,4-hexadiyne-1,6-diol, 16.74 g of (±)-2-cyclopenten-4-one-1-ol chloroacetic acid ester and 36 ml of dichloromethane, and the resulting mixture was heated to 40° C. to turn it into a solution. After adding 45 ml of petroleum ether at 35° to 40° C., the mixture was cooled to 20° C. and kept at the same temperature for 2 hours.

The deposited white crystals were filtered off to obtain 13.85 g of a complex of (+)-1,6-diphenyl-1,6-di(o-chlorophenyl)-2,4-hexadiyne-1,6-diol with (+)-2-cyclopenten-4-one-1-ol chloroacetic acid ester.

m.p., 108°–110° C.

$[\alpha]_D^{20}$, +110.8° (c=1, methanol)

Procedure was carried out in the same manner as in Example 26 except that the complex of (+)-1,6-diphenyl-1,6-di(o-chlorophenyl)-2,4-hexadiyne-1,6-diol with (+)-2-cyclopenten-4-one-1-ol n-butyric acid ester was replaced by the complex of (+)-1,6-diphenyl-1,6-di(o-chlorophenyl)-2,4-hexadiyne-1,6-diol with (+)-2-cyclopenten-4-one 1-ol chloroacetic acid ester {$[\alpha]_D^{20}$, +110.8° (c=1, methanol)}, to obtain 9.1 g of a 1:2 complex of (+)-1,6-diphenyl-1,6-di(o-chlorophenyl)-2,4-hexadiyne-1,6-diol with acetone as a white crystal.

m.p., 100.5° C.

This crystal was treated in the same manner as in Example 26 to obtain 7.32 g of (+)-1,6-diphenyl-1,6-di(o-chlorophenyl)-2,4-hexadiyne-1,6-diol (percent recovery, 100%).

m.p., 131.5° C.

$[\alpha]_D^{20}$, +124.3° (c=1, methanol)

The filtrate obtained when the above complex was collected by filtration was concentrated by removing the solvent, and the residue was purified by column chromatography using a 2:10 mixed solvent of ethyl acetate and toluene to obtain 2.63 g of (+)-2-cyclopenten-4one-1-ol chloroacetic acid ester (percent recovery, 9.8%).

m.p., 73°-74.5° C.

$[\alpha]_D^{20}$, +103° (c=1, methanol)

EXAMPLE 34

To the same flask as used in Example 26 were added 14.49 g of (+)-1,6-diphenyl-1,6-di(o-chlorophenyl)-2,4-hexadiyne-1,6-diol, 15.3 g of (±)-2-cyclopenten-one-1-ol methoxyacetic acid ester and 12 ml of dichloromethane, and the resulting mixture was heated to 40° C. to turn it into a solution. After adding 30 ml of petroleum ether at 36° to 40° C., the mixture was cooled to 20° C. and kept at the same temperature for 2 hours.

The deposited white crystals were filtered off to obtain 16.7 g of a complex of (+)-1,6-diphenyl-1,6-di(o-chlorophenyl)-2,4-hexadiyne-1,6-diol with (+)-2-cyclopenten-4-one-1-ol methoxyacetic acid ester.

m.p., 120°-121° C.

$[\alpha]_D^{20}$, +117.1° (c=1, methanol)

Procedure was carried out in the same manner as in Example 26 except that the complex of (+)-1,6-diphenyl-1,6-di(o-chlorophenyl)-2,4-hexadiyne-1,6-diol with (+)-2-cyclopenten-4-one-1-ol n-butyric acid ester was replaced by the complex of (+)-1,6-diphenyl-1,6-di(o-chlorophenyl)-2,4-hexadiyne-1,6-diol with (+)-2-cyclopenten-4-one-1-ol methoxyacetic acid ester {$[\alpha]_D^{20}$, +117.1° (c=1, methanol)}, to obtain 9.15 g of a 1:2 complex of (+)-1,6 diphenyl-1,6-di(o-chlorophenyl)-2,4-hexadiyne-1,6-diol with acetone as a white crystal.

m.p., 100.3° C.

This crystal was treated in the same manner as in Example 26 to obtain 7.35 g of (+)-1,6-diphenyl-1,6-di(o-chlorophenyl)-2,4-hexadiyne-1,6-diol (percent recovery, 99.4%).

m.p., 131.5° C.

$[\alpha]_D^{20}$, +124.5° (c=1, methanol)

The filtrate obtained when the above complex was collected by filtration was treated in the same manner as in Example 26 to obtain 2.59 g of (+)-2-cyclopenten-4-one-1-ol methoxyacetic acid ester (percent recovery, 99.4%).

$[\alpha]_D^{20}$, +97.4° (c=1, methanol)

EXAMPLE 35

To the same flask as used in Example 26 were added 14.49 g of (+) 1,6-diphenyl-1,6-di(o-chlorophenyl)-2,4-hexadiyne-1,6-diol, 15.3 g of (±)-2-cyclopenten-4-one-1-ol methoxyacetic acid ester and 10 ml of toluene, and the resulting mixture was heated to 40° C. to turn it into a solution. After adding 30 ml of petroleum ether at 36° to 40° C., the mixture was cooled to 20° C. and kept at the same temperature for 2 hours.

The deposited white crystals were filtered off to obtain 11.5 g of a complex of (+)-1,6-diphenyl-1,6-di(o-chlorophenyl)-2,4-hexadiyne-1,6-diol with (+)-2-cyclopenten-4-one-1-ol methoxyacetic acid ester.

m.p., 120°-121° C.

$[\alpha]_D^{20}$, +117.1° (c=1, methanol)

What is claimed is:

1. A method for producing an optically active 2-cyclopenten-4-one-1-ol ester represented by the formula (I),

wherein R represents a saturated or unsaturated aliphatic hydrocarbon residue optionally substituted with a halogen atom or a methoxy or ethoxy group, and * represents an asymmetric carbon, which comprises contacting a 2-cyclopenten-4-one-1-ol ester represented by the formula (III),

with an optically active 1,6-diphenyl-2,4-hexadiyne, 1,6-diol derivative represented by the formula (II),

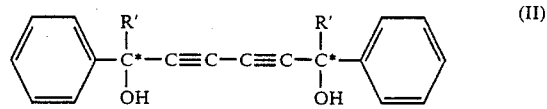

wherein R' represents a halogenated phenyl, lower alkylphenyl, naphthyl or tertiary lower alkyl group, and * represents an asymmetric carbon, in a organic solvent to obtain an optically active cyclopentenone ester complex of the optically active 2-cyclopenten-4-one-1-ol ester of formula (I) with the optically active 1,6-diphenyl-2,4-hexadiyne-1,6-diol derivative of formula (II), and decomposing the optically active cyclopenteneone ester complex and recovering the optically active 2-cyclopenten-4-one-1-ol ester.

2. A method according to claim 1, wherein R is a $C_2-C_5$ chain or branched alkyl group.

3. A method according to claim 1, wherein R is a $C_1-C_3$ alkyl group substituted with a halogen atom.

4. A method according to claim 1, wherein R is a methoxymethyl, methoxyethyl, methoxypropyl, ethoxymethyl or ethoxyethyl group.

5. A method according to claim 1, wherein R' is a halogenated phenyl group.

6. A method according to claim 1, wherein the organic solvent is benzene, toluene, xylene or chlorobenzene.

7. A method according to claim 1, wherein the organic solvent is chloroform, carbon tetrachloride, dichloromethane, dichloroethane, pentane, hexane, heptane, petroleum ether or ligroin.

8. A method according to claim 1, wherein the organic solvent is ethyl ether, acetonitrile or ethyl acetate.

9. A method according to claim 1, wherein formation of the complex is carried out at a temperature in a range of from −20° to 80° C.

10. A method according to claim 1, wherein the amount of the optically active compound contained in the 2-cyclopenten-4-one-1-ol ester used for formation of the complex is in a range of from 1 to 2 times by equivalent based on the 1,6-diphenyl-2,4-hexadiyne-1,6-diol derivative.

11. A method according to claim 1, wherein the optically active 2-cyclopenten-4-one-1-ol ester and the optically active 1,6-diphenyl-2,4-hexadiyne-1,6-diol derivative form a 1:1 complex.

12. A method according to claim 1, wherein the optically active 1,6-diphenyl-2,4-hexadiyne-1,6-diol derivative has a (+)-optical rotation, and the ester obtained has an R(+)-conformation.

13. A method according to claim 1, wherein the optically active 1,6-diphenyl-2,4-hexadiyne-1,6-diol derivative has a (−)-optical rotation, and the ester obtained has an S(−)-conformation.

14. A method for producing an optically active 2-cyclopenten-4-one-1-ol ester represented by the formula (I),

wherein R represents a saturated or unsaturated aliphatic hydrocarbon residue optionally substituted with a halogen atom or a methoxy or ethoxy group, and * represents an asymmetric carbon, which comprises contacting a 2-cyclopenten-4-one-1-ol ester represented by the formula (III),

with an optically active 1.6-diphenyl-2,4-hexadiyne, -1,6-diol derivative represented by the formula (II),

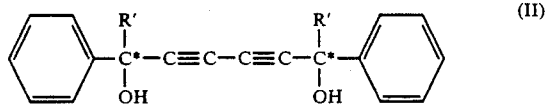

wherein R' represents a halogenated phenyl, lower alkylphenyl, naphthyl or tertiary lower alkyl group and * represents an asymmetric carbon, in an organic solvent to obtain an optically active cyclopentenone ester complex of the optically active 2-cyclopenten-4-one-1-ol ester of formula (I) with the optically active 1,6-diphenyl-2,4-hexadiyne-1,6-diol derivative of formula (II); decomposing the optically active cyclopenteneone ester complex by heating the complex under reduced pressure and recovering the optically active 2-cyclopenten-4-one-1-ol ester.

15. A method for producing an optically active 2-cyclopenten-4-one-1-ol ester represented by the formula (I),

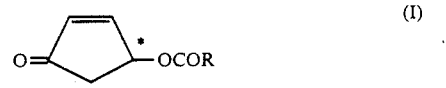

wherein R represents a saturated or unsaturated aliphatic hydrocarbon residue optionally substituted with a halogen atom or a methoxy or ethoxy group, and * represents an asymmetric carbon, which comprises contacting a 2-cyclopenten-4-one-1-ol ester represented by the formula (III).

with an optically active 1,6-diphenyl-2,4-hexadiyne-1,6diol derivative represented by the formula (II),

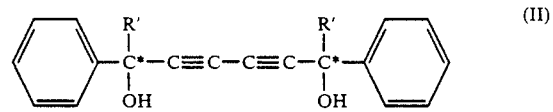

wherein R' represents a halogenated phenyl, lower alkylphenyl, naphthyl or tertiary lower alkyl group, and * represents an asymmetric carbon, in an organic solvent to obtain an optically active cyclopentenone ester complex of the optically active 2-cyclopenten-4one-1-ol ester of formula (I) with the optically active 1,6-diphenyl-2,4-hexadiyne-1,6-diol derivative of formula (II); decomposing the optically active cyclopentenone ester complex by treating the complex with a treating agent selected from the group consisting of a ketone, cyclic ether, heterocyclic amine, aliphatic amine, alicyclic amine or cyclic amide or dimethyl sulfoxide and N,N-dimethylformamide in an organic solvent to liberate the optically active cyclopentenone ester from the complex and to form a crystalline complex of the optically active 1,6-diphenyl-2,4-hexadiyne-1,6-diol derivative (II) with the treating agent, separating the organic solvent containing liberated optically active cyclopentenone ester from the resultant crystalline complex, and recovering the liberated optically active 2-cyclopenten-4-one-1-ol ester (I) from the organic solvent.

16. A method according to claim 15, wherein the ketone is acetone, methyl ethyl ketone, cyclopentaneone or cyclohexanone.

17. A method according to claim 15, wherein the cyclic ether is tetrahydrofuran or dioxane.

18. A method according to claim 15, wherein the heterocyclic amine is pyridine or quinoline.

19. A method according to claim 15, wherein the cyclic amide is pyrrolidone.

20. A method according to claim 15, wherein the amount of the treating agent is 2 to 30 times by equivalent based on the optically active 1,6-diphenyl -2,4-hexadiyne-1,6-diol derivative (II).

21. An optically active 2-cyclopenten-4-one-1-ol ester represented by the general formula (I),

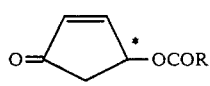 (I)

wherein R represents a $C_1$–$C_3$ alkyl group substituted with a methoxy or ethoxy group and * represents an asymmetric carbon.

22. A compound according to claim 21 having an R(+)-conformation.

23. A compound according to claim 21 having an S(−)-conformation.

24. A method for producing an optically active cyclopentenone ester complex of an optically active 2-cyclopenten-4-one-1ol ester represented by the general formula (I)

 (I)

wherein R represents a saturated or unsaturated aliphatic hydrocarbon residue optionally substituted with a halogen atom or a methoxy or ethoxy group, and * represents an asymmetric carbon, with an optically active 1,6-diphenyl-2,4-hexadiyne-1,6-diol derivative represented by the general formula (II),

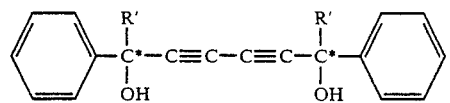 (II)

wherein R' represents a halogenated phenyl, lower alkyl-phenyl, naphthyl or tertiary lower alkyl group, and * represents an asymmetric carbon, which comprises contacting a 2-cyclopenten-4-one-1ol ester represented by the general formula (III),

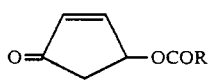 (III)

with the optically active 1,6-diphenyl-2,4-hexadiyne-1,6diol derivative of formula (III) in an organic solvent.

25. A method according to claim 24, wherein R is a $C_2$–$C_5$ chain or branched alkyl group.

26. A method according to claim 24, wherein R is a $C_1$–$C_3$ alkyl group substituted with a halogen atom.

27. A method according to claim 24, wherein R is a methoxymethyl, methoxyethyl, methoxypropyl, ethoxymethyl or ethoxyethyl group.

28. A method according to claim 24, wherein R' is a halogenated phenyl group.

29. A method according to claim 24, wherein the organic solvent is benzene, toluene, xylene or chlorobenzene.

30. A method according to claim 24, wherein the organic solvent is chloroform, carbon tetrachloride, dichloromethane, dichloroethane, pentane, hexane, heptane, petroleum ether or ligroin.

31. A method according to claim 24, wherein the organic solvent is ethyl ether, acetonitrile or ethyl acetate.

32. A method according to claim 24, wherein formation of the complex is carried out at a temperature in a range of from −20° to 80° C.

33. A method according to claim 24, wherein the amount of the optically active compound contained in the 2-cyclopenten-4-one-1-ol ester used for formation of the complex is in a range of from 1 to 2 times by equivalent based on the 1,6-diphenyl-2,4-hexadiyne-1,6-diol derivative.

34. A method according to claim 24, wherein the optically active 2-cyclopenten-4-one-1-ol ester and the optically active 1,6-diphenyl-2,4-hexadiyne-1,6-diol derivative form a 1:1 complex.

35. A method according to claim 24, wherein the optically active 1,6-diphenyl-2,4-hexadiyne-1,6-diol derivative has a (−)-optical rotation, and the ester which forms said ester complex therewith has an R(+)-conformation 36. A method according to claim 24, wherein the optically active 1,6-diphenyl-2,4-hexadiyne-1,6-diol derivative has a (−)-optical rotation, and the ester which forms said ester complex therewith has an S(−)-conformation.

37. An optically active cyclopentenone ester complex of an optically active 2-cyclopenten-4-one-1-ol ester represented by the general formula (I),

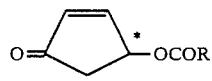 (I)

wherein R represents a saturated or unsaturated aliphatic hydrocarbon residue which may or may not be substituted with a halogen or methoxy or ethoxy atom, and * represents an asymmetric carbon,
with an optically active 1,6-diphenyl-2,4-hexadiyne-1,6-diol derivative represented by the general formula (II),

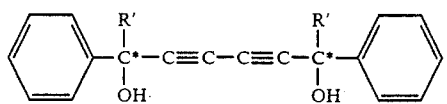 (II)

wherein R' represents a halogenated phenyl, lower alkylphenyl, naphthyl or tertiary lower alkyl group, and * represents an asymmetric carbon.

38. A compound according to claim 37, wherein R is a $C_2$–$C_5$ chain or branched alkyl group.

39. A compound according to claim 37, wherein R is a $C_1$–$C_3$ alkyl group substituted with a halogen atom.

40. A compound according to claim 37, wherein R is a methoxymethyl, methoxyethyl, methoxypropyl, ethoxymethyl or ethoxyethyl group.

41. A compound according to claim 37, wherein R' is a halogenated phenyl group.

42. A compound according to claim 37, wherein the optically active 1,6-diphenyl-2,4-hexadiyne-1,6-diol derivative has a (+)-optical rotation, and the ester which forms said ester complex therewith has an R(+)-conformation.

43. A compound according to claim 37, wherein the optically active 1,6-diphenyl-2,4-hexadiyne-1,6-diol derivative has a (−)-optical rotation, and the ester which forms said ester complex therewith has an S(−)-conformation.

* * * * *